(12) United States Patent
Chen et al.

(10) Patent No.: US 8,309,135 B2
(45) Date of Patent: Nov. 13, 2012

(54) RADIOACTIVE GOLD NANOPARTICLES AND METHODS OF MAKING AND USING THEM

(75) Inventors: Jen-Kun Chen, Hsinchu (TW); Jinn-Jer Peir, Hsinchu (TW); Mei-Ya Wang, Taoyuan (TW); Chih-Hui Liu, Pingtung (TW); Fong-In Chou, Hsinchu (TW); Chung-Shi Yang, Taichung (TW); Mo-Hsiung Yang, Hsinchu County (TW); Mei-Hui Shih, Taichung (TW)

(73) Assignees: National Health Research Institutes, Miaoli County (TW); National Tsing Hua University, Hsinchu (TW)

( * ) Notice: Subject to any disclaimer, the term of this patent is extended or adjusted under 35 U.S.C. 154(b) by 443 days.

(21) Appl. No.: 12/636,798

(22) Filed: Dec. 14, 2009

(65) Prior Publication Data

US 2010/0150828 A1  Jun. 17, 2010

Related U.S. Application Data

(60) Provisional application No. 61/138,511, filed on Dec. 17, 2008.

(51) Int. Cl.
*A61K 9/14* (2006.01)

(52) U.S. Cl. ........................................... 424/489

(58) Field of Classification Search ........................ None
See application file for complete search history.

(56) References Cited

U.S. PATENT DOCUMENTS 7,767,063 B2 * 8/2010 Risen et al. ............... 204/157.15
2007/0051202 A1   3/2007 Raghuraman et al.

OTHER PUBLICATIONS

Raghuraman Kannan,*Valerie Rahing, Cathy Cutler, Ravi Pandrapragada. Kavita K. Katti, Vijaya Kattumuri, J. David Robertson, Stan J. Casteel, Silvia Jurisson, Charles Smith, Evan Boete, and Kattesh V. Katti*: (2006)Nanocompatible chemistry toward fabrication of target-specific gold nanoparticles J.Am.Chem. Soc 128(35) 11342-11343.

Nripen Chancla, Ravi Shukla, Kattesh V. Katti* and Raghuraman Kannan* (2009) Gastrin Releasing Protein Receptor specific gold nanorods;breast and prostate tumor avid nanovectors for molecular imaging Nanolett., 9(5) 1798-1805.

Katti, K.V. et al., (2006) "Hybrid gold nanoparticles in molecular imaging and radiotherapy" Czechoslovak J. of Physics vol. 56 Suppl. D.

Mohamed K. Khan et al.. (2008) "Fabrication of {198Au0} radioactive composite nanodevices and their use for nano-brachytherapy" Nanomedicine 4(1): 57-69.

Yunfeng Lu et al., "Aerosol-assisted selfassembly of mesostructured spherical nanoparticles" Nature vol. 398 , Mar. 18, 1999 223-226.

* cited by examiner

*Primary Examiner* — Paul Dickinson
(74) *Attorney, Agent, or Firm* — Hsiu-Ming Saunders; Intellectual Property Connections, Inc.

(57) ABSTRACT

Methods of preparing a composition comprising non-ionic, radioactive gold nanoparticles (R-GNPs) are disclosed. The method comprises: a) providing an aqueous composition comprising gold (Au-197) ions in the absence of a template; and b) exposing the aqueous composition in the absence of the template to neutron irradiation to generate the composition comprising the non-ionic R-GNPs. Alternatively, the method comprises: a) providing an aqueous composition comprising gold (Au-197) nanoparticles (GNPs) in the absence of a template; and b) exposing the aqueous composition comprising the GNPs in the absence of the template to neutron irradiation and thereby generating the composition comprising the non-ionic R-GNPs. Compositions that comprises mesoporous silica nanoparticles (MSNs) and non-ionic R-GNPs encapsulated within pores and/or channels and further anchored to the surfaces of the MSNs, and methods of making the same are also disclosed.

22 Claims, 7 Drawing Sheets

FIG. 1

| Sample | a | b | c | d | e | f | g | h |
|---|---|---|---|---|---|---|---|---|
| Exposure Time (min) | 1 | 5 | 15 | 30 | 1 | 5 | 15 | 30 |
| Size (nm) | NA | 110.8 | 93.0 | 104.8 | NA | 62.2 | 62.0 | 67.0 |
| PDI | NA | 0.118 | 0.086 | 0.077 | NA | 0.165 | 0.125 | 0.168 |
| Absorbance@ 520nm (AU) | 0.011 | 0.061 | 0.042 | 0.125 | 0.009 | 0.246 | 0.206 | 0.241 |
| Specific Activity (micro-Ci/mL) | 0.2 | 1.0 | 3.0 | 6.6 | 0.6 | 3.0 | 8.6 | 19.0 |

RADIOACTIVE GOLD NANOPARTICLES AND METHODS OF MAKING AND USING THEM

REFERENCE TO RELATED APPLICATION

The present application claims the priority to U.S. Provisional Application Ser. No. 61/138,511, filed Dec. 17, 2008, which is herein incorporated by reference in its entirety.

FIELD OF THE INVENTION

The present invention relates generally to gold nanoparticles, and more specifically to compositions comprising radioactive gold nanoparticles.

BACKGROUND OF THE INVENTION

Radioactive gold seeds, which are metallic gold formulations without surface coating or modification, have been used for treating cancer since the 1950s. They were used as permanent surgical implants for brachytherapy. To improve the performance and extend the applications of gold seeds, strategies have been used to reduce the size of invasive implants to nanometer-scaled particles and to anchor, immobilize, or incorporate non-gold molecules or non-gold nano-materials.

To study efficacy and potential side effects for animals and humans, the size, shape, and surface chemistry of GNPs must be carefully defined in terms of the biological properties, including absorption, distribution, metabolism and excretion. A need exists in the art to address the establishment of a platform for observing and tracing GNPs in vivo.

SUMMARY OF THE INVENTION

The invention relates to methods of making radioactive gold nanoparticles (R-GNPs) which require exposing non-radioactive precursors to neutron irradiation in a nuclear reactor. Naturally abundant gold (Au-197) within GNPs or GNP composites can be transformed into R-GNPs (Au-198), which then serve as a gamma-radiation source (412 keV) and a beta particle (electron) emitter (maximum energy: 0.96 MeV). The gamma photons and beta particles enable tracing R-GNPs in vivo as well as providing therapeutic benefits in killing tumor cells. The methods of making radioactive GNP composites in combination with radio-diagnosis and radiotherapy can bring a niche in development of multifunctional radioactive nano-pharmaceuticals.

The method makes non-ionic R-GNPs (Au-198) of a defined size, shape and surface property, with or without surface modifications. The GNPs may be encapsulated within other nano-structured materials, irradiated by neutron flux in a nuclear reactor to produce multifunctional nano-sized carriers comprising non-ionic R-GNPs. The resulting R-GNPs, sterilized after neutron activation, can be directly used for medical applications such as tracing, diagnostic, and therapeutic purposes in animals and humans.

In one aspect, the invention relates to a method of preparing a composition comprising non-ionic, radioactive gold nanoparticles (R-GNPs) from nonradioactive gold ions. The method comprises the steps of: a) providing a solution comprising gold (Au-197) ions; and b) exposing the solution to neutron irradiation to generate a composition comprising non-ionic R-GNPs.

In one embodiment of the invention, prior to the exposing step the method further comprises the step of performing a reduction reaction by reacting the gold (Au-197) ions with a reducing agent to form gold (Au-197) nanoparticles (GNPs) in the solution. The reducing agent may be an amine or a citrate salt to form amine-protected or citrate-protected GNPs in the solution.

Alternatively, prior to the exposing step the method further comprises the step of performing a reduction reaction by exposing the gold (Au-197) ions in the solution to X-ray or gamma ray irradiation to form gold (Au-197) nanoparticles (GNPs) in the solution.

In another embodiment of the invention, prior to the exposing step further comprising the step of admixing a non-gold material with the solution, wherein the non-gold material is to be conjugated to the surfaces of the non-ionic R-GNPs generated in the exposing step, thereby generating a composition comprising non-ionic R-GNPs, of which the surfaces are modified with the non-gold material.

Further in another embodiment of the invention, the solution of Au-197 ions in step (a) above further comprises mesoporous silica nanoparticles (MSNs) with multiple pores and/or channels for encapsulating and/or anchoring the non-ionic R-GNPs to be generated in the exposing step, and thereby generating a composition comprising non-ionic R-GNPs encapsulated within and/or anchored to the MSNs.

In another aspect, the invention relates to a method of preparing a composition comprising non-ionic R-GNPs from nonradioactive GNPs. The method comprises the steps of a) providing a solution which comprises a composition comprising gold nanoparticles (GNPs, Au-197); and b) exposing the solution comprising GNPs to neutron irradiation to generate a composition comprising non-ionic R-GNPs. The surface of the GNP in step (a) is with or without modifications by a non-gold material.

In one embodiment of the invention, prior to step (a) immediately above the method further comprises the step of i) providing a solution comprising gold (Au-197) ions; and ii) performing a reduction reaction by reacting the gold (Au-197) ions with a reducing agent to form a solution comprising GNPs (Au-197). The reducing agent may be an amine or a citrate salt to form amine-protected or citrate-protected GNPs in the solution.

Alternatively, a reduction reaction may be performed by exposing the gold (Au-197) ions in the solution to X-ray or gamma ray irradiation to form GNPs (Au-197) in the solution.

In another embodiment of the invention, prior to the exposing step the method further comprises the step of: admixing a non-gold material with the solution comprising the amine or citrate-protected GNPs formed from the reduction step, wherein the non-gold material is to be conjugated to the surfaces of the non-ionic R-GNPs generated in the exposing step, thereby generating a composition comprising non-ionic R-GNPs, of which the surfaces are modified with the non-gold material.

In another embodiment of the invention, the Au-197 GNP solution in step (a) immediately above further comprises MSNs, which contain multiple pores and/or channels encapsulating and/or anchoring the GNPs, and thereby in the exposing step generating a composition comprising non-ionic R-GNPs encapsulated within and/or anchored to the MSNs.

In another embodiment of the invention, the method as mentioned above may further comprise the step of conjugating at least one non-gold material to the surfaces of the non-ionic R-GNPs, thereby generating a composition comprising non-ionic R-GNPs, of which the surfaces are modified with the non-gold material.

Further in another embodiment of the invention, the non-gold material may be selected from the group consisting of citrate salts, alkyl amines, silica, polyethylene glycol (PEG), methoxy-terminated polyethylene glycol (PEG) derivatives, carboxy-terminated PEG derivatives, amine-terminated PEG derivatives, synthetic polymers, carbohydrates, proteins, peptides, amino acids, nucleic acids and fatty acids.

Yet in another embodiment of the invention, the exposing step in the method above may further comprise the step of adjusting the duration and/or flux of the neutron irradiation to control the radioactivity level and/or size of the R-GNPs in the composition.

Further in another aspect, the invention relates to a composition comprising: a) mesoporous silica nanoparticles (MSNs), which contain multiple pores and/or channels; and b) non-ionic R-GNPs; wherein the R-GNPs are encapsulated within and/or anchored to the MSNs. The surface of the R-GNP encapsulated within and/or anchored to the MSN may be modified with at last at least one non-gold material.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "adjusting the flux of neutron irradiation" shall generally mean "adjusting the density and rate of neutron irradiation."

As used herein, amines are organic compounds which contain and are often actually based on one or more atoms of nitrogen. In an amine, one or more of the hydrogen atoms from ammonia are replaced by organic substituent like alkyl (alkane chain) and aryl (aromatic ring) groups.

As used herein, a "silicate precursor" shall generally means a compound selected from the group consisting of sodium silicate and a compound of the formula:

(I)

wherein $R'_1$, $R'_2$, $R'_3$ and $R'_4$ are the same or different, and represent, independently of each other, an alkyl or an aryl group. In one embodiment, $R'_1$, $R'_2$, $R'_3$ and $R'_4$ are $C_{1-6}$ alkyl or $C_{1-6}$ aryl. For example, the silicate precursor may be at least one selected from the group consisting of tetraethoxysilane (TEOS), tetramethoxysilane (TMOS), and sodium silicate.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Generation of Radioactive Bare Gold Nanoparticles

Figure 1:
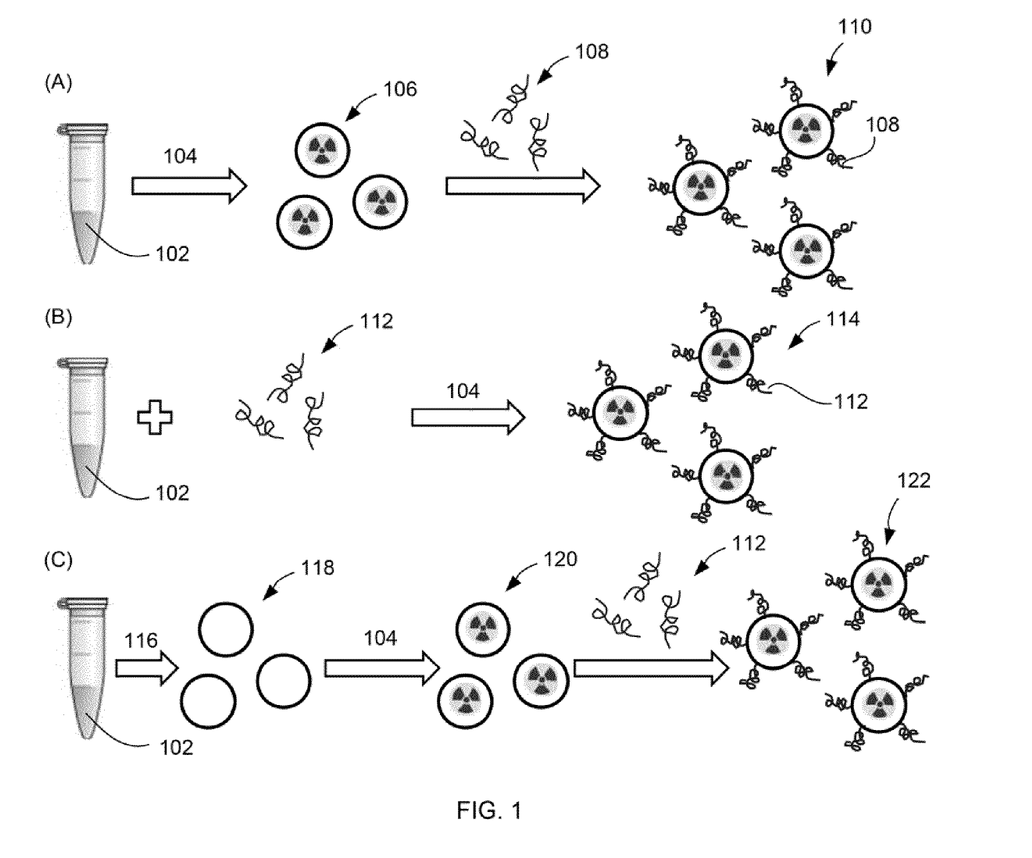
FIG. 1A illustrates generation of non-ionic, radioactive gold nanoparticles (R-GNPs) from gold-197 ions according to one embodiment of the invention.
FIG. 1B illustrates generation of non-ionic R-GNPs with surfaces conjugated to non-gold materials from gold-197 ions according to another embodiment of the invention.
FIG. 1C illustrates generation of non-ionic R-GNPs with surfaces conjugated to non-gold materials from gold-197 ions according to further another embodiment of the invention.

FIG. 1A illustrates that a method for making radioactive bare gold nanoparticles ($^{198}$Au nanoparticles) 106 does not involve any radioactive precursor or any template. Non-radioactive hydrogen tetrachloroaurate hydrate 102 ($H^{197}AuCl_4 \cdot xH_2O$) (Aldrich, USA) was used as a gold precursor. A solution (30 mL) containing gold ions 102 (0.1~1000 mM) was stirred for 15 min at room temperature for homogenization and equilibration, then irradiated in a nuclear reactor (Tsing Hua Open-pool Reactor, National Tsing Hua University, Hsinchu, Taiwan), which could provide a controllable neutron source 104, e.g., $3.4 \times 10^{12}$ n·cm$^{-2}$·sec$^{-1}$ for thermal neutron and $1.2 \times 10^{12}$ n·cm$^{-2}$·sec$^{-1}$ for fast neutron (the term "n" represents the number of neutrons). The non-radioactive gold ions 102 were reduced to gold nanoparticles (GNPs) and simultaneously activated to become radioactive in a single 5-minute-step. The method generates radioactive bare gold nanoparticles (R-GNPs) 106 with a defined size distribution and controllable radioactivity. Afterwards, a non-gold material 108 may be admixed with the bare R-GNPs 106 to alter, modify, or enhance their physical, chemical, and/or biological properties, resulting in surface-modified R-GNPs 110.

Figure 2:
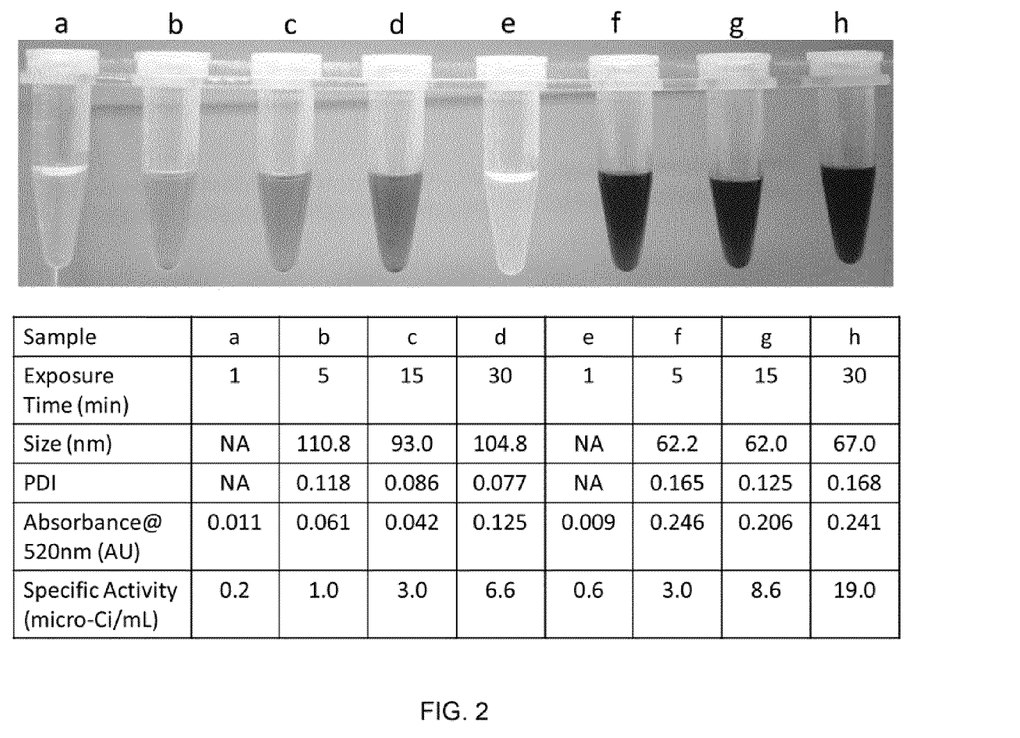
FIG. 2 shows bare (or naked) R-GNPs generated by a one-step reaction, in which the HAuCl$_4$ solution was exposed to various neutron flux to generate R-GNPs of different sizes. Samples in a, b, c, d received thermal neutron flux: $1.4 \times 10^{12}$ n·cm$^{-2}$·sec$^{-1}$; fast neutron flux: $3.4 \times 10^{11}$ n·cm$^{-2}$·sec$^{-1}$; samples in e, f, g, h received thermal neutron flux: $3.4 \times 10^{12}$ n·cm$^{-2}$·sec$^{-1}$; fast neutron flux: $1.2 \times 10^{12}$ n·cm$^{-2}$·sec$^{-1}$.
Figure 3:
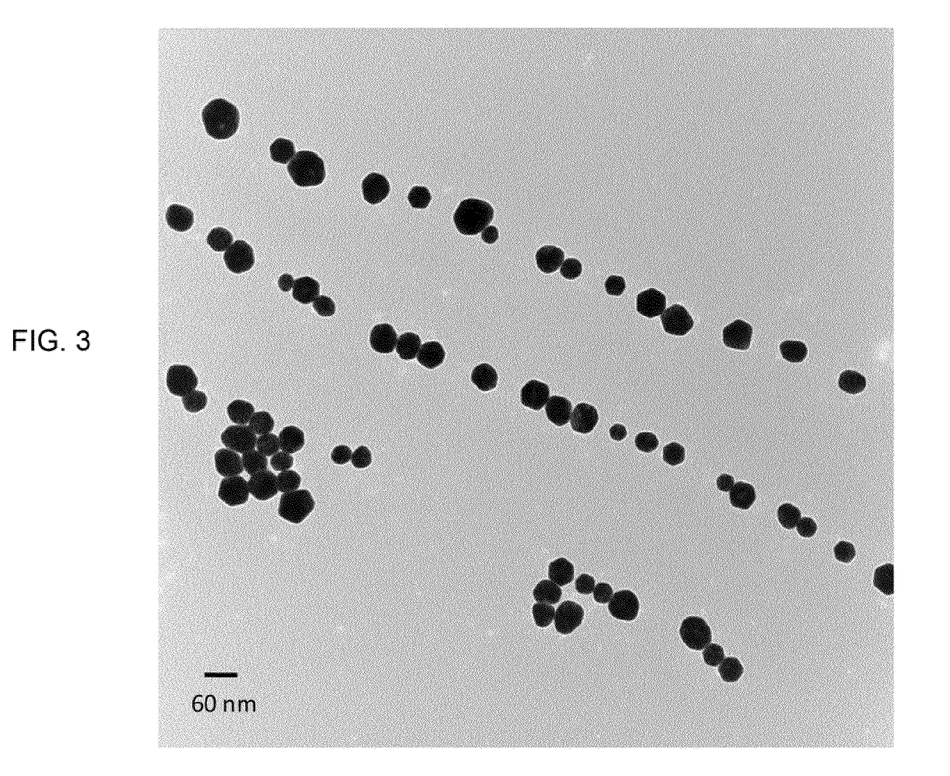
FIG. 3 is a TEM image of radioactive bare GNPs prepared by neutron irradiation of non-radioactive HAuCl$_4$ in a nuclear reactor.

The formation of bare R-GNPs was affected by the following factors: the concentration of non-radioactive HAuCl$_4$, neutron flux and exposure time in the nuclear reactor. FIG. 2 shows R-GNPs generated from 1.0 mM of HAuCl$_4$ using two levels of neutron flux. The bare R-GNPs were prepared by a one-step process, in which the HAuCl$_4$ solution (1.0 mM) was exposed to various neutron flux to generate R-GNPs of different sizes. The higher the neutron flux was, the smaller the particle size was generated. The polydisperse index (PDI) indicated that the R-GNPs had a tight size distribution. The increase in absorbance at 520 nm, which represents the surface plasmon band of GNPs, clearly demonstrated the formation of GNPs. The specific activity of R-GNPs could be manipulated as it was correlated with the exposure time in the nuclear reactor. The FIG. 2 shows that an increase in neutron flux decreased the size of R-GNPs. Adjusting the exposure time in the nuclear reactor, e.g., ranging from 1 to 30 min, could lead to various levels of radioactivity for R-GNPs (FIG. 2). FIG. 3 shows the shape and physical size of R-GNPs, as determined by a transmission electron microscope (TEM).

Example 2

Preparation of PEG-Conjugated R-GNPs from Au-197 Ions

As illustrated in FIG. 1B, the method of making radioactive GNPs (R-GNPs) 114 with surfaces modified by an organic material 112 does not involve any template. To synthesize polyethylene glycol (PEG)-conjugated R-GNPs 114, non-radioactive HAuCl$_4$ (10 mL, 10 mM) 102 and PEG6000 (PEG6K; 10 mM) 112 were combined to form a mixture, which were irradiated 104 in a nuclear reactor with thermal neutrons ranging from $1.0 \times 10^{11}$~$1.5 \times 10^{13}$ n·cm$^{-2}$·sec$^{-1}$ and fast neutrons ranging from $1.0 \times 10^{11}$~$1.7 \times 10^{13}$ n·cm$^{-2}$·sec$^{-1}$, ("n" is the number of neutrons). Adjusting irradiation duration could give rise to PEG modified R-GNPs 114 with desired various specific activities. An exposure time of from 10 to 120 min led to generation of PEG6K-conjugated R-GNPs 114 having specific activities of 13.3 to 187 μCi/mg gold (Table 1). Other PEGs which may conjugate to the surfaces of R-GNPs include, but not limited to, PEG1K, PEG2K, PEG3K, PEG4K, PEG5K, PEG6K, PEG8K, PEG 10K, PEG20K, and PEG30K.

TABLE 1

| PEG6K-conjugated R-GNPs | | | | | |
|---|---|---|---|---|---|
| | Neutron Irradiation Time (min) | | | | |
| | 10 | 20 | 30 | 60 | 120 |
| Formulations | Solution | solution | Solution | solution | solution |
| Specific Activity (uCi/mL) | 20 | 38 | 56 | 150 | 280 |
| Specific Activity (uCi/mg of gold) | 13.3 | 25.3 | 37.3 | 100 | 187 |

Figure 4:
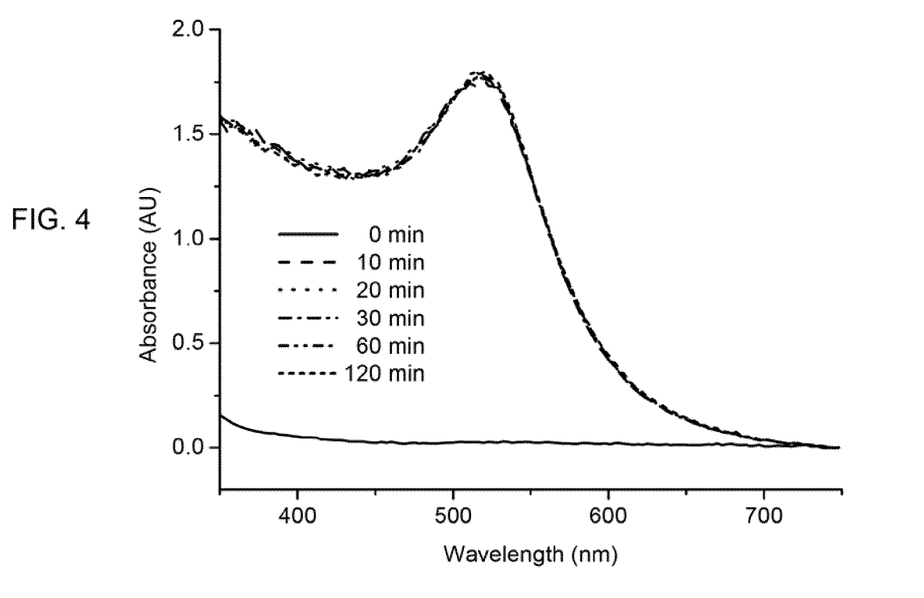
FIG. 4 shows the UV-visible spectra of radioactive PEG6K-GNPs prepared by exposing a mixture of PEG and non-radioactive HAuCl$_4$ to neutron irradiation in a nuclear reactor for various durations as indicated.

FIG. 4 shows the UV-visible spectra of un-irradiated solution and PEG6K-conjugated R-GNPs after neutron irradiation for 10~120 min. The spectra for PEG6K-conjugated R-GNPs were superimposed perfectly both in the width and height of the peak. The spectra represent the surface plasmon band of the GNPs, confirming the physico-chemical property of the R-GNPs. The results indicated that the concentration and physico-chemical properties of the PEG6K-conjugated GNPs were preserved after exposure to neutron irradiation in the nuclear reactor.

PEG derivatives such as methoxy-terminated PEG thiol, carboxy-terminated PEG thiol, and amine-terminated PEG thiol may be used to conjugate to R-GNPs using the method as described above. Other non-gold molecules for modifying the surfaces of R-GNPs include, but not limited to, synthetic polymers, carbohydrates, proteins, nucleic acids, fatty acids and other organic acids.

Example 3

Preparation of Citrate-Protected R-GNPs

Figure 5A:
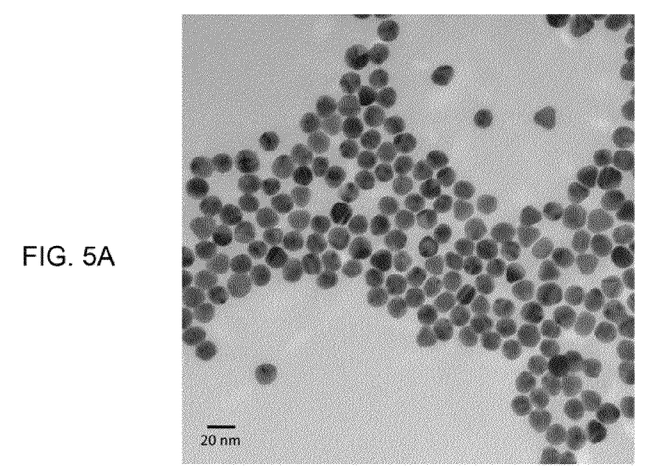
FIG. 5A is a TEM image of citrate-protected R-GNPs with an average size of 12.9±1.2 nm (480 particles).
Figure 5B:
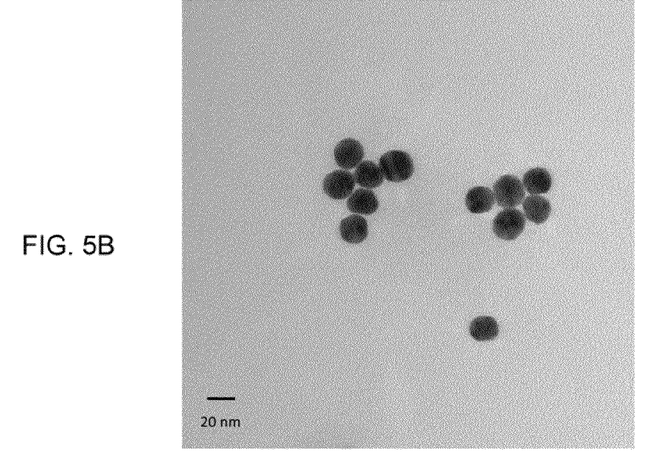
FIG. 5B is a TEM image of citrate-protected R-GNPs with an average size of 17.7±2.9 nm (381 particles).
Figure 6:
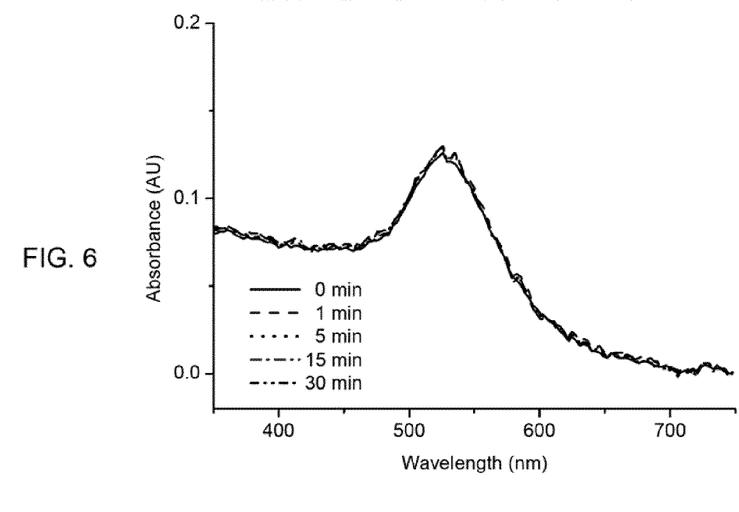
FIG. 6 shows UV-visible spectra of citrate-protected R-GNPs prepared by exposing non-radioactive GNPs to neutron irradiation in a nuclear reactor for various durations as indicated.

As illustrated in FIG. 1C, non-radioactive HAuCl$_4$ (500 mL, 1.6 mM) 102 was brought to boil in a round-bottom flask under vigorous stirring [Lin et al. (2002) "Recognition of potassium ion in water by 15-crown-5 functionalized gold nanoparticles" *Anal. Chem.* 74, 330-335.]. Sodium citrate (Na$_3$C$_3$H$_5$O(COO)$_3$, 38.8 mM, 50 mL) 116 was rapidly poured into the HAuCl$_4$ solution 102 to reduce gold ions to citrate-protected GNPs 118, which directly correlated with the color change from pale yellow to burgundy. The size of citrate-protected GNPs 118 was controllable by adjusting the molar ratio of non-radioactive HAuCl$_4$ 102 to sodium citrate 116. This solution was boiled for additional 10 min and then cooled with continuously stirring. After the solution reached room temperature, the aqueous citrate-protected GNPs 118 were exposed to neutron irradiation 104 in a nuclear reactor ($3.4 \times 10^{12}$ n·cm$^{-2}$·sec$^{-1}$ of thermal neutron flux and $1.5 \times 10^{13}$ n·cm$^{-2}$·sec$^{-1}$ of fast neutron flux). Adjusting the irradiation time could give various specific activities (activity per milliliter) to citrate-protected R-GNPs 120. Within 1~30 min of irradiation duration, the specific activity of the citrate-protected R-GNPs 120 varied from 0.6 to 10.4 micro-Ci/mL. FIGS. 5A-5B show the citrate-protected R-GNPs with size of 12.9±1.2 and 17.7±2.9 nm, respectively. The UV-vis spectra in FIG. 6 allow comparisons of the surface plasmon band of GNPs (17.7±2.9 nm) after exposed to various durations of neutron irradiation to characterize the properties of citrate-protected R-GNPs. The spectra were perfectly superimposed with that of non-radioactive citrate-protected GNP, which indicated the particle size and concentration of citrate-protected R-GNPs remained the same after the neutron irradiation.

Example 4

Preparation of PEG-Conjugated R-GNPs from R-GNPs

Radioactive GNPs (R-GNPs), either bare or citrated protected, can serve as a precursor for making surface-modified R-GNPs via conjugation with a PEG derivative, such as methoxy-terminated PEG thiol (e.g., mPEG5K-SH, MW ~5000 Daltons), carboxy-terminated PEG thiol (e.g., cPEG5K-SH), and amine-terminated PEG thiol (e.g., aPEG5K-SH).

For example, mPEG5K-SH (0.5 mL, 10 mM) was added to a solution containing citrate-protected R-GNPs for 0.3 to 24 hours. The slurry of mPEG5K-GNPs was collected after centrifugation at 15700 g for 15 min at 10° C. The method could produce various kinds of surface-modified R-GNPs in large scale with defined diameters and in any forms, including solution, slurry and powder. PEG derivatives including, but not limited to, mPEG thiol, cPEG thiol and aPEG thiol with molecular weights raging from about 1K to about 30K Daltons are all able to covalently bind to the surfaces of R-GNPs for generating PEG-derivative conjugated R-GNPs.

Alternatively, radioactive mPEG5K thiol conjugated R-GNPs may be prepared from pre-made non-radioactive mPEG5K-GNPs by exposing the latter to irradiation in a nuclear reactor for $3.4 \times 10^{12}$ n·cm$^{-2}$·sec$^{-1}$ of thermal neutron flux and $1.5 \times 10^{13}$ n·cm$^{-2}$·sec$^{-1}$ of fast neutron flux. Table 2 lists the specific activity of 20 nm GNPs conjugated with different PEG derivatives after 2 hrs of irradiation time.

TABLE 2

| | R-GNPs conjugated with | | |
|---|---|---|---|
| | mPEG2K-SH | mPEG5K-SH | cPEG5K-SH |
| Formulations | Slurry | Slurry | Slurry |
| Irradiation Time (hrs) | 2 | 2 | 2 |
| Specific Activity (mCi/mL) | 2.54 | 1.89 | 2.34 |
| Specific Activity (mCi/mg of gold) | 0.379 | 0.300 | 0.266 |

Example 5

Preparation of Protein-Conjugated R-GNPs

The bare or citrate-protected R-GNP can be used as a starting material for making a protein-conjugated R-GNP. Tumor necrosis factor-alpha (TNFα; 10 μL, 1.0 mg/mL) was added to the R-GNP solution (1 mL, pH 11, titrated with 1N NaOH) and allowed to react at 4° C. for 30 min with gentle vortexing. After aging at 4° C. for another 30 min, the mixture was centrifuged at 6000 rpm, 4° C. for 15 min. The supernatant was subjected to a further centrifugation at 10000 rpm. The pellets of the first and second centrifugations were pooled together to harvest TNFα-conjugated R-GNPs. Concentrated TNFα-conjugated R-GNPs were made into a slurry for storage and further applications.

Example 6

Preparation of R-GNPs Conjugated with Multiple Non-Gold Materials

The bare or citrate-protected R-GNP can be used as a starting material for making R-GNPs with surfaces conjugated to at least two kinds of non-gold materials, such as mPEG5K and TNFα. For example, mPEG5K thiol (10 μL, 5.2 mM) and TNFα (1 μL, 1.0 μg/μL) were added to the R-GNP solution (1 mL, pH 11, titrated with 1N NaOH) and allowed to react at 4° C. for 15 min with gentle vortex. After aging at 4° C. for another 15 min, the mixture was centrifuged at 6000 rpm, 4° C. for 15 min. The supernatant was subjected to a further centrifugation at 10000 rpm. The pellets of the first and second centrifugations were combined, and made into a slurry (i.e., concentrated mPEG5K-R-GNPs-TNFα) for storage and further applications. Table 3 shows the particle size and zeta potential of R-GNPs at every step of the process of making mPEK5K-R-GNP-TNFα. The zeta potential moved from extremely minus toward nearly neutral, which is a remarkable index and can be utilized to evaluate the completeness of the conjugation reaction.

TABLE 3

| | Zeta Potential (mV) | Size by DLS (nm) |
|---|---|---|
| R-GNP (pH = 6) | −41.9 | 35.8 |
| R-GNP (pH = 11) | −57.6 | 52.8 |
| Radioactive mPEK5K-S-GNP-TNFα | −6.5 | 75.1 |

Example 7

Preparation of Radioactive Silica-Coated-GNPs (R-SGNPs)

Silica-coated gold nanoparticles (SGNPs) can be covalently conjugated with specific functional groups on molecules of interest, allowing generation of composite nanoparticles. In addition, SGNPs can enhance the stability against aggregation in physiological environments. Radioactive silica-coated GNPs (R-SGNPs) are useful for tracing in vivo without the need for a fluorescent tag.

An aqueous solution containing amine-protected gold nanoparticle was prepared by mixing non-radioactive chloroauric acid ($H^{197}AuCl_4$, 90 ml, 1.0 mM) and oleyl amine (1.0 ml, 1.0 mM) with mild heating at 50° C. to yield stable amine-protected GNPs. The alkylamine (e.g., oleyl amine)-reduced GNPs were subjected for centrifugation at 10000 rpm for 30 min. The pellet fraction was washed with double deionized water (dd $H_2$) to remove free alkylamine molecules. The pellet can be re-dispersed in polar (e.g., dd $H_2O$) or in non-polar solvents.

SGNPs were synthesized through the formation of water-in-cyclohexane reverse microemulsion. Briefly, Igepal CO-520 (0.35 mL, as a surfactant) was added to alkylamine-protected GNP solution (6 mL). Ammonia solution (0.2 mL) and tetraethylorthosilicate (TEOS, 20 µL, as a silicate precursor) were added consecutively with stirring to form a transparent red solution of reverse microemulsion. SGNPs with an overall particle size (core-shell structured) of about 35 nm were obtained via 15 h of reaction at room temperature. To control the thickness of silica coating, increasing the concentration of TEOS and/or prolonging the reaction time were necessary. Ethanol was added to disrupt the reverse microemulsion once the desired particle size had been achieved. After the ethanol extraction, SGNPs were collected by centrifugation and re-dispersed in water or ethanol.

Figure 7:
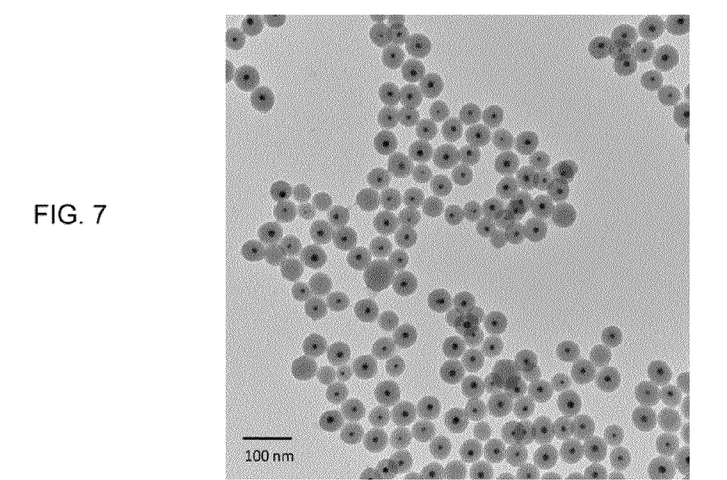
FIG. 7 is a TEM image showing radioactive silica-coated gold nanoparticles (R-SGNPs).

To obtain radioactive silica-coated-GNPs (R-SGNPs) with the size around 35 nm (FIG. 7), the above SGNPs were exposed to irradiation in a nuclear reactor for 2 hours. The specific activity was within the range of 60~114 micro-Ci/mL under a controllable neutron flux, which includes thermal neutrons ranging from $1.0 \times 10^{11}$~$1.5 \times 10^{13}$ n·cm$^{-2}$·sec$^{-1}$ and fast neutrons ranging from $1.0 \times 10^{11}$~$1.7 \times 10^{13}$ n·cm$^{-2}$·sec$^{-1}$.

Example 8

Preparation of Mesoporous Silica Nanoparticle (MSN)-Anchored R-GNPs

Two different methods were employed to synthesize MSN-anchored R-GNPs (MSN-R-GNPs). In a first method, core-shell structured silica-coated-GNPs (SGNPs, used as silicate precursor) are incorporated in the process of forming MSNs, and the resulting MSN-GNPs are then made into MSN-R-GNPs. Briefly, SGNPs (0.32 g, from Example 7) were added to an alkaline mixture (50 mL, pH>10) of $SiO_2$, cetyltrimethyl ammonium bromide (CTAB), NaOH, $H_2O$ and ethanol in a molar ratio of 1:0.11:0.24:395:36 at room temperature. After 15 min of equilibration, the solution was placed in an autoclave at 100° C. under a static condition for 24 h. The alkaline dissolves the silica, rendering the GNPs uncoated with silica. The MSN-anchored GNPs were recovered by centrifugation, washed with dd $H_2O$, and dried in an oven at 50° C. for 12 h. The residual CTAB was removed with an air stream heated to 540° C. for 6 h. The MSN-GNPs were exposed to neutrons in a nuclear reactor to introduce radioactivity using thermal neutrons ($1.0 \times 10^{11}$~$1.5 \times 10^{13}$ n·cm$^{-2}$·sec$^{-1}$) and fast neutrons ($1.0 \times 10^{11}$~$1.7 \times 10^{13}$ n·cm$^{-2}$·sec$^{-1}$). Adjusting irradiation time led to different levels of specific activities (activity per mg) for MSN-R-GNPs. The specific activity ranged from about 1 to 400 micro-Ci/mg after irradiation in a nuclear reactor for 1~360 min.

In a second method, pre-made MSNs may be added into non-radioactive gold ions and then exposed to neutron irradiation in a nuclear reactor to obtain a nanocomposite material that encapsulate and/or anchor R-GNPs, i.e., MSN-R-GNPs. In this situation, the pre-made MSN serves as an inorganic anchor to form MSN-anchored R-GNPs. To synthesize the MSN, a mixture of $SiO_2$, cetyltrimethyl ammonium bromide (CTAB), NaOH, $H_2O$ and ethanol in a molar ratio of 1:0.11:0.24:395:36 was prepared as a gel form, allowed to reach equilibration for 15 min, and then autoclaved at 100° C. under a static condition for 24 h. The final solid material, i.e., MSNs, was recovered as described above.

Non-radioactive gold ions (0.1~100 mM), such as $HAuCl_4 \cdot xH_2O$, gold (III) acetate, gold (I) acetate, gold (III) hydroxide, gold (I) monohydroxide, may be used to mix with the above pre-made MSN anchor (1~1000 mg) to synthesize MSN-anchored R-GNPs. By neutron irradiation at $3.4 \times 10^{12}$ n·cm$^{-2}$·sec$^{-1}$ for thermal neutron and $1.2 \times 10^{12}$ n·cm$^{-2}$·sec$^{-1}$ for fast neutron, non-radioactive gold ($^{197}Au$) ions were reduced to GNPs and simultaneously activated the GNPs to become R-GNPs in a single 30-minute-step.

Figure 8:
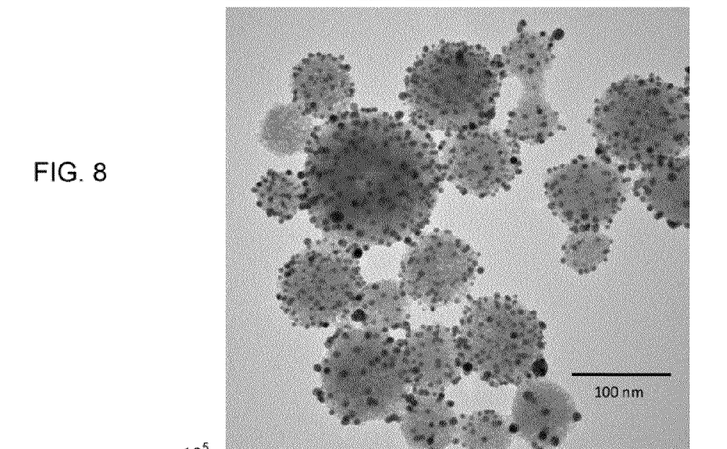
FIG. 8 is a TEM image showing mesoporous silica nanoparticle (MSN)-anchored R-GNPs.

FIG. 8 shows a TEM image of R-GNPs anchored to MSNs. The sherical MSN served as an anchor to R-GNPs, forming MSNs-anchored R-GNPs (MSN-GNPs). The image shows that R-GNPs were encapsulated within the pores and/or channels of MSNs. In addition, R-GNPs appeared to associate with the surfaces of MSNs, which suggested that GNPs might form within the porous structures near the surfaces and grew outward. Some GNPs appeared to crystallize deeper in the pores/channels of the MSNs.

Example 9

Validation of R-GNP Formation

Figure 9:
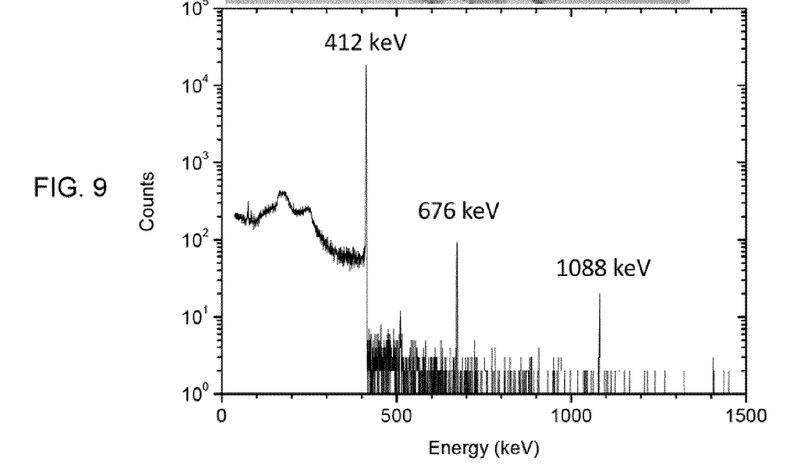
FIG. 9 is a gamma photon energy spectrum of radioactive mPEG5K-GNP-TNF, indicating the formation of Au-198.

To confirm radioactive gold (Au-198) was indeed generated by the above methods, mPEG-R-GNP-TNFα were characterized using a high purity germanium (HPGe) detector (GC1020, CANBERRA, USA). As shown in FIG. 9, the energy spectrum exhibited characteristic peaks at 412, 676 and 1088 keV with an abundance of 99.4%, 0.5% and 0.1%, respectively. This was in accordance with the theoretical gamma photon emissions of Au-198. The results verified the radiochemical properties of the material generated (i.e., the radioactive Au-198).

Example 10

Cytotoxic Effects of R-GNPs on Cancer Cells

Figure 10:
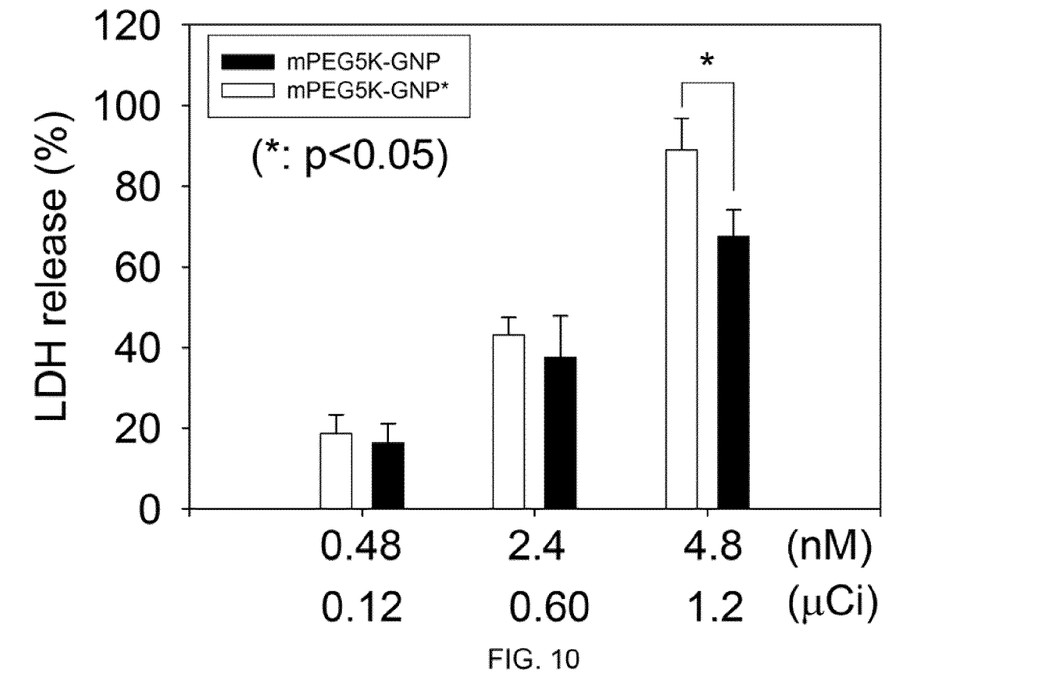
FIG. 10 shows the results of LDH release assay to evaluate the R-GNP efficacy in killing cancer cells.

H460 human large cell carcinoma cells (Bioresource Collection and Research Center, Hsinchu, Taiwan) were grown in RPMI-1640 medium containing fetal bovine serum (10%, v/v), L-glutamine (2 mM), HEPES (10 mM), sodium pyruvate (1 mM), glucose (4.5 g/L) and sodium bicarbonate (1.5 g/L) at 37 'C and 5% $CO_2$. The cells were detached with trypsin (0.05%)/EDTA 1.0 (0.53 mM) in Hanks' balanced salt solution. A lactate dehydrogenase (LDH) assay [Uboldi et al. (2009) "Gold nanoparticles induce cytotoxicity in the alveolar type-II cell lines A549 and NCIH441" *Particle and fibre toxicology* 6, 18.] was conducted to evaluate the cytotoxicity of R-GNPs in comparison with non-radioactive GNPs. H460 cells were seeded onto 24-well plates ($2 \times 10^4$ cells/well), grown overnight and treated with mPEG5K-R-GNPs (radioactive), mPEG5K-GNPs (non-radioactive) or the medium alone (control) for 24 h at 37° C. The supernatants (50 µL/well) were collected for the LDH assay (Clontech, US). The results were expressed as a mean increase in LDH release relative to the control (i.e., experimental LDH release−control LDH release)/control LDH release×100%±standard error of the mean (SEM). FIG. 10 shows that at a concentration of 4.8 nM of gold nanoparticles there was a significant difference between R-GNPs and GNPs in LDH release from the cancer cells. The R-GNPs contained 1.2 μCi of radioactivity, which caused more of LDH release than a comparable concentration of GNPs. Since the amount of LDH release is an indicator of cell membrane damage, the results demonstrated that radioactive mPEG5K-GNPs with 1.2 μCi of radioactivity (Au-198) could lead to a significant damage to cancer cells.

Example 11

R-GNPs Suppress Tumor Growth In Vivo

Figure 11:
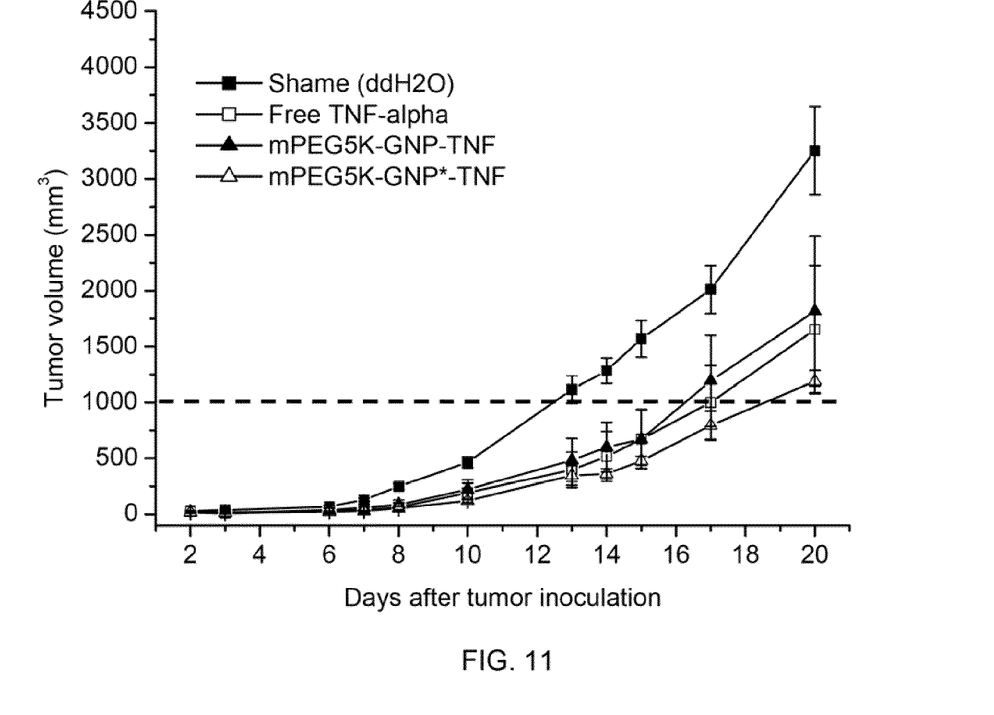
FIG. 11 is a graph of tumor size growth curves showing R-GNPs suppress tumor growth in human large-cell lung carcinoma H460-bearing animal model. The data were expressed as mean±standard error of the mean (SEM).

To evaluate the effects of R-GNPs on tumor suppression, tumor-bearing mice were prepared by subcutaneous transplantation of H460 (5×10$^4$) human large-cell lung carcinoma cells into male NU/NU mice (6 weeks old, purchased from BioLASCO, Taiwan) at the dorsal region of the right thigh. The tumor volume was measured with a vernier scale caliper and the value calculated using the formula of length$^2$×width/2. The tumor-bearing mice were divided into four groups, with 4 animals per group, and each animal was administered a single dose of a test agent via the caudal vein at 2 days post inoculation with H460 tumor cells as follows: (1) control group, treated with dd H$_2$O; (2) TNFα group, treated with free form of TNFα (7.5 μg/mouse); (3) non-radioactive GNP (around 20 nm) group, treated with PEG5K-GNP-TNFα (estimated 7.5 TNFα/mouse); and (4) R-GNP group, treated with PEG5K-R-GNP-TNFα (estimated 7.5 μgTNFα plus 80 μCi/mouse). FIG. 11 shows the tumor growth curve of each animal group. The times required for the tumor to grow bigger than 1000 mm$^3$ in the control, TNFα, non-radioactive GNP and R-GNP groups were 13, 17, 17, and 20 days post inoculation, respectively, which were appropriate indicators for evaluating the tumor suppression efficacy of a single dose treatment with R-GNPs.

Example 12

Tracing R-GNPs in Living Animals

The gamma rays emitted by R-GNPs are valuable for tracing particles and diagnostic purposes. Single photon emission computed tomography (SPECT) was used to trace R-GNPs in living animals. Mice (BALB/c, 6 weeks old, male) were anesthetized with Zoletil® (12.5 mg/kg) and Xylazine (5 mg/kg) through intraperitoneal injection. Radioactive mPEG2K-GNPs (200 μCi in 50% PBS; particle around 20 nm) were injected into mice through the caudal vein. The images of R-GNPs were acquired by a single camera head SPECT imaging system (E. CAM plus HD3 Detector, SIEMENS) equipped with a pinhole collimator (5 mm I.D.). Mice were positioned on their backs with legs extended and 2.0 cm below the pinhole collimator for whole body imaging. To present an in viva image of R-GNPs, gamma ray events were accumulated until a total of 150 k counts were collected.

Figures 12A, 12B:
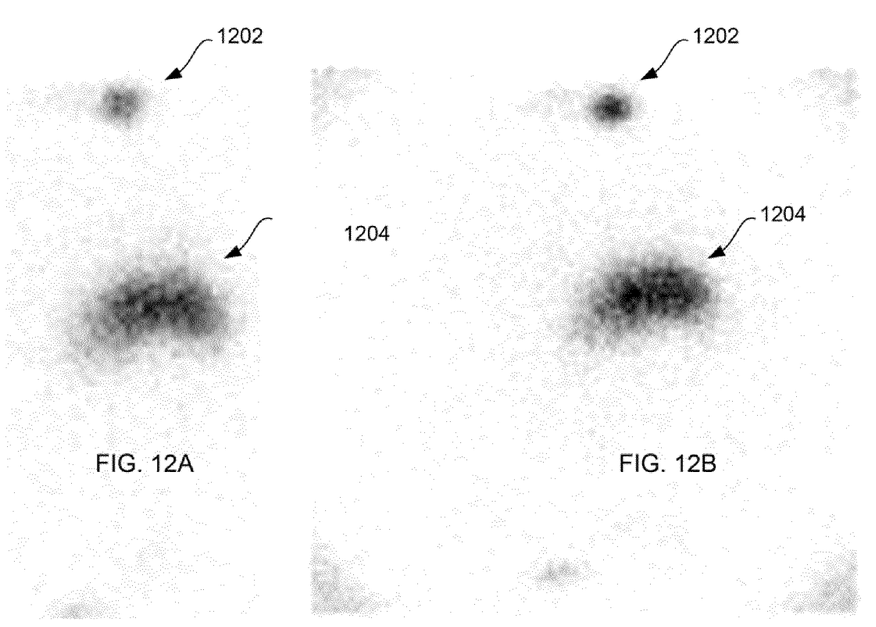
FIG. 12A is a single photon emission computed tomography (SPECT) image of a mouse taken at 2 minutes after caudal vein administration of R-GNPs, mPEG2K-GNP.
FIG. 12B is a single photon emission computed tomography (SPECT) image of the mouse of FIG. 12A taken at 15 minutes after caudal vein administration of the R-GNP, mPEG2K-GNP.

FIGS. 12A and 12B are SPECT images of a BALB/c mouse taken at about 2 and 15 min post caudal vein administration of 20 nm radioactive mPEG2K-GNPs, showing the bio-distribution of these particles. The image spot indicated by the arrow 1202 represents the nose of the mouse because it was generated by a marker positioned adjacent to the mouse nose. The image spot indicated by the arrow 1204 represents the liver of the mouse, as determined by the distance from the marker at the nose 1202. The results indicated that radioactive mPEG2K-GNPs were dominantly delivered to the mouse liver 1204 at about 2 min (FIG. 12A) and 15 min (FIG. 12B) post i.v. injections. The gold distribution in liver 1204 was subsequently confirmed by a metal analysis using inductively coupled plasma mass spectrometry (ICP-MS). The size and surface chemistry of the particles can impact the absorption, distribution, metabolism, and excretion (abbreviated as "ADME") fates of R-GNPs. In addition to being utilized in SPECT imaging, R-GNPs may also be used to therapeutic purposes because of beta particle (0.96 MeV) emission from Au-198.

By using R-GNPs, the characteristic 412 keV gamma ray (from Au-198) can provide convenience for tracing GNPs in vivo. Similar to previous studies on radioactive gold brachytherapy, the Au-198 containing GNPs can emit beta particles (electrons) leading to therapeutic feasibility in the microenvironment of tumors.

In summary, the invention relates to methods of making non-ionic R-GNPs (Au-198). Non-radioactive GNPs (Au-197) can be prepared with precisely defined and controllable parameters. The defined shape GNPs with adjustable size and modified surfaces may be employed to anchor, immobilize or incorporate with other kinds of non-gold molecules and/or non-gold nanomaterials to create core-shell structures. GNPs can be encapsulated by materials such as liposome, polylactic-co-glycolic acid (PLGA), chitosan and geletin for preparing organo-inorganic hybrid nanoparticles. After the fabrication of composite nanoparticles, the samples are subsequently treated with neutron irradiation in a nuclear reactor. Through neutron activation, Au-197 can capture a neutron and be transformed into Au-198. With proper control of the nuclear reactor and recipes for making nanoparticles, the inventors have succeeded in preserving the physical and chemical properties of radioactive gold containing nanocomposites similar to the GNPs prior to neutron activation. The 412 keV gamma ray emitted from Au-198 allows for tracing the distribution and excretion of nano-composites via detection of radioactivity and SPECT imaging system. The non-ionic R-GNPs become sterilized after neutron activation. The R-GNPs possess multiple functions for bio-medical applications including tracing, diagnostic and therapeutic capability, giving insights into nano-pharmaceuticals.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A method of preparing a composition comprising non-ionic, radioactive gold nanoparticles (R-GNPs), comprising the steps of:
   (a) providing a solution comprising gold (Au-197) ions in the absence of a template; and
   (b) exposing the solution in the absence of the template to neutron irradiation to generate the composition comprising the non-ionic R-GNPs.

2. The method of claim 1, prior to the exposing step further comprising the step of:
   (i) performing a reduction reaction by exposing the gold (Au-197) ions in the solution to X-ray or gamma ray irradiation to form gold (Au-197) nanoparticles (GNPs) in the solution.

3. The method of claim 1, prior to the exposing step further comprising the step of:
   (i) performing a reduction reaction by reacting the gold (Au-197) ions with a reducing agent to form GNPs (Au-197) in the solution.

4. The method of claim 3, wherein the reducing agent is an amine or a citrate salt to form amine-protected or citrate-protected GNPs in the solution.

5. The method of claim 4, prior to the exposing step further comprising the step of:
   admixing a non-gold material with the solution, wherein the non-gold material conjugates to the surfaces of the non-ionic R-GNPs and thereby generating the composition comprising the non-ionic R-GNPs, of which the surfaces are modified with the non-gold material.

6. The method of claim 5, wherein the non-gold material is at least one selected from the group consisting of citrate salts, alkyl amines, silica, polyethylene glycol (PEG), methoxy-terminated polyethylene glycol (PEG) derivatives, carboxy-terminated PEG derivatives, amine-terminated PEG derivatives, synthetic polymers, carbohydrates, proteins, peptides, amino acids, nucleic acids and fatty acids.

7. The method of claim 1, wherein the solution in step (a) further comprises mesoporous silica nanoparticles (MSNs) containing multiple pores and/or channels and the exposing step generates the composition comprising the non-ionic R-GNPs, in which the R-GNPs are encapsulated within the pores and/or channels and are further anchored to the surfaces of the MSNs.

8. The method of claim 1, further comprising the step of:
   (c) conjugating at least one non-gold material to the surfaces of the non-ionic R-GNPs, thereby generating the composition comprising the non-ionic R-GNPs, of which the surfaces are modified with the non-gold material.

9. The method of claim 1, prior to the exposing step further comprising the step of:
   admixing a non-gold material with the solution, wherein the non-gold material is conjugated to the surfaces of the non-ionic R-GNPs generated in the exposing step, thereby generating the composition comprising the non-ionic R-GNPs, of which the surfaces are modified with the non-gold material.

10. The method of claim 1, wherein the exposing step further comprises the step of adjusting the duration and flux of the neutron irradiation to control the radioactivity level and/or size of the R-GNPs in the composition.

11. A method of preparing a composition comprising non-ionic R-GNPs from gold (Au-197) nanoparticles, comprising the steps of
   (a) providing an aqueous composition comprising the gold nanoparticles (GNPs) in the absence of a template; and
   (b) exposing the aqueous composition comprising the GNPs in the absence of the template to neutron irradiation and thereby generating the composition comprising the non-ionic R-GNPs.

12. The method of claim 11, wherein the surfaces of the GNPs in step (a) are modified with at least one non-gold material.

13. The method of claim 11, prior to step (a) further comprising the steps of:
   (i) providing a solution comprising gold (Au-197) ions in the absence of the template; and
   (ii) performing a reduction reaction by exposing the gold (Au-197) ions in the solution to X-ray or gamma ray irradiation in the absence of the template to form the aqueous composition comprising the GNPs (Au-197).

14. The method of claim 11, prior to step (a) further comprising the steps of
   (i) providing a solution comprising gold (Au-197) ions in the absence of the template; and
   (ii) performing a reduction reaction by reacting the gold (Au-197) ions with a reducing agent to form the aqueous composition comprising the GNPs (Au-197).

15. The method of claim 14, wherein the reducing agent is an amine or a citrate salt to form amine-protected or citrate-protected GNPs in the aqueous composition.

16. The method of claim 15, prior to the exposing step further comprising the step of:
   (iii) admixing a non-gold material with the aqueous composition comprising, the amine or citrate-protected GNPs formed from the reduction step, wherein the non-gold material conjugates to the surfaces of the non-ionic R-GNPs and thereby generating the composition comprising the non-ionic R-GNPs, of which the surfaces are modified with the non-gold material.

17. The method of claim 11, wherein the aqueous composition in step (a) further comprises MSNs containing multiple pores and/or channels encapsulating and/or anchoring the GNPs, and the exposing step generates the composition comprising the non-ionic R-GNPs, in which the R-GNPs are encapsulated within the pores and/or channels and are further anchored to the surfaces of the MSNs.

18. The method of claim 11, further comprising the step of:
   (c) conjugating at least one non-gold material to the surfaces of the non-ionic R-GNPs, thereby generating the composition comprising the non-ionic R-GNPs, of which the surfaces are modified with the non-gold material.

19. The method of claim 12, wherein the non-gold material is at least one selected from the group consisting of citrate salts, alkyl amines, silica, polyethylene glycol (PEG), methoxy terminated polyethylene glycol (PEG) derivatives, carboxy-terminated PEG derivatives, amine-terminated PEG derivatives, synthetic polymers, carbohydrates, proteins, peptides, amino acids, nucleic acids and fatty acids.

20. The method of claim 16, wherein the non-gold material is at least one selected from the group consisting of citrate salts, alkyl amines, silica, polyethylene glycol (PEG), methoxy terminated polyethylene glycol (PEG) derivatives, carboxy-terminated PEG derivatives, amine-terminated PEG derivatives, synthetic polymers, carbohydrates, proteins, peptides, amino acids, nucleic acids and fatty acids.

21. A composition comprising:
   (a) mesoporous silica nanoparticles (MSNs), which contain multiple pores and/or channels; and
   (b) non-ionic R-GNPs;
   wherein the R-GNPs are encapsulated within the pores and/or channels of the MSNs and are further anchored to the surfaces of the MSNs.

22. The composition of claim 21, wherein the surfaces of R-GNPs are modified with at least one non-gold material.

* * * * *